United States Patent [19]

Linden et al.

[11] Patent Number: 4,981,610

[45] Date of Patent: Jan. 1, 1991

[54] REAGENT FOR RENDERING BIOLOGICAL MEDIA TRANSPARENT AND ITS ANALYTICAL APPLICATIONS

[75] Inventors: Guy Linden, Heillecourt; Gérard M. Humbert, Jarville La Mai; Rosalie Kouomegne, Nancy; Marie F. Guingamp, Heillecourt, all of France

[73] Assignee: Universite De Nancy I, Nancy Cedex, France

[21] Appl. No.: 52,390

[22] Filed: May 21, 1987

[30] Foreign Application Priority Data

May 21, 1986 [FR] France .................................. 8607236

[51] Int. Cl.$^5$ ...................... G01N 21/00; G01N 33/04
[52] U.S. Cl. ................................... 252/408.1; 436/20; 436/22; 436/23; 436/174; 252/174.22
[58] Field of Search ........................ 252/408.1, 174.22; 436/20, 22, 23, 174

[56] References Cited

U.S. PATENT DOCUMENTS

| 961,564 | 6/1910 | Wendler et al. ...................... 436/22 |
| 3,853,465 | 12/1974 | Rush et al. . | |
| 3,960,493 | 1/1976 | Beitz et al. ............................ 436/22 |
| 4,184,848 | 1/1980 | Batz et al. . | |
| 4,282,001 | 8/1981 | Klose et al. ......................... 436/174 |

FOREIGN PATENT DOCUMENTS 2084726 8/1982 United Kingdom .

OTHER PUBLICATIONS

Nakai et al., "Spectrophotometric Determination of Protein and Fat in Milk Simultaneously", *Journal of Dairy Science*, vol. 53, No. 3.

Sager et al., "A Study of the Schain Butterfat Test", Published Oct. 1951.

*Primary Examiner*—Robert L. Stoll
*Assistant Examiner*—Valerie Fee
*Attorney, Agent, or Firm*—Oblon, Spivak, McClelland, Maier & Neustadt

[57] ABSTRACT

The reagent of the invention consists of a combination of an aliphatic ketone, a detergent, a base and a denaturating agent for rendering transparent a protein and lipid containing mixture.

15 Claims, 4 Drawing Sheets

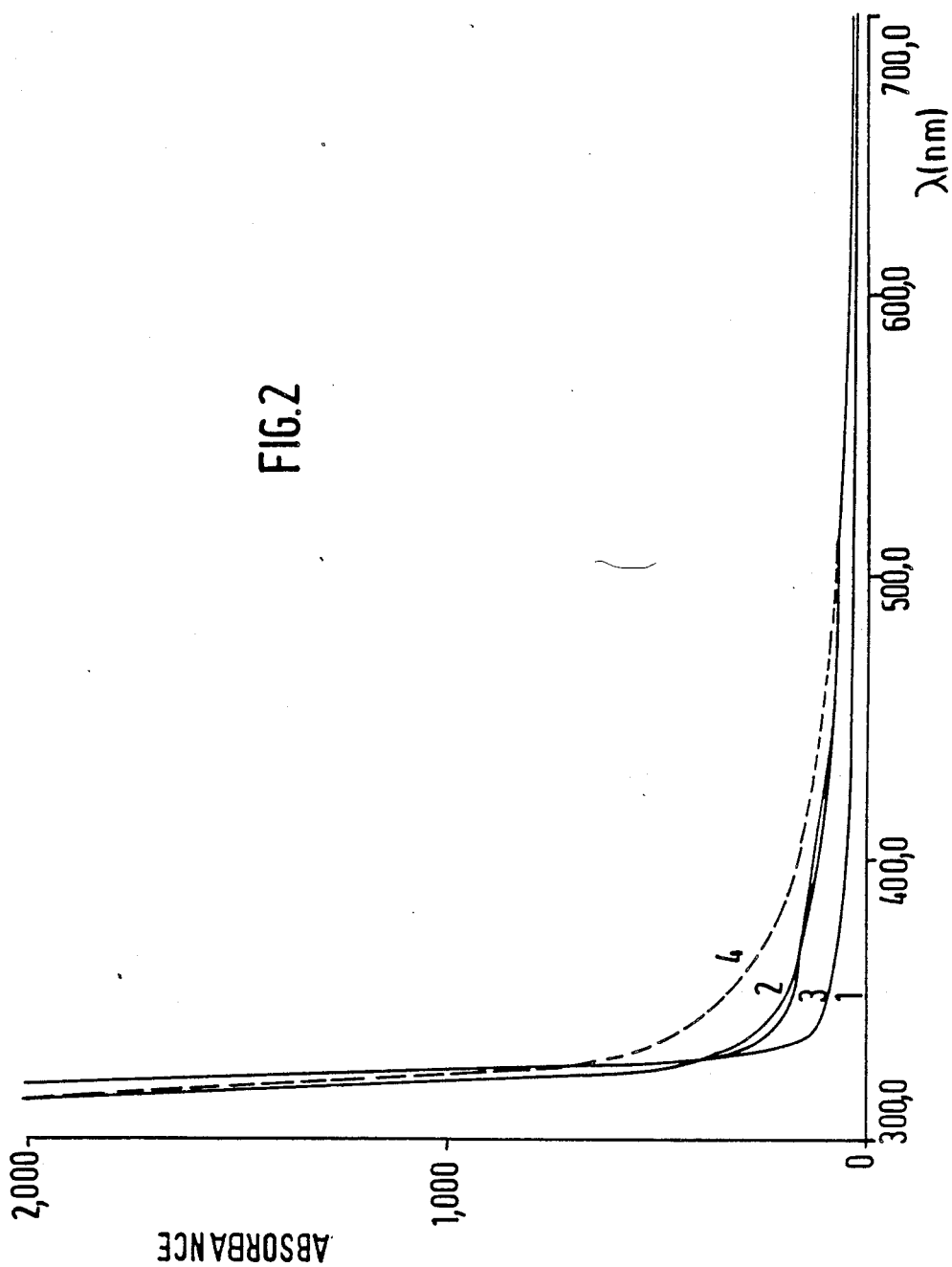

REAGENT FOR RENDERING BIOLOGICAL MEDIA TRANSPARENT AND ITS ANALYTICAL APPLICATIONS

The subject of the invention is a reagent for rendering biological media transparent and its analytical applications.

It is known that many biological media exhibit a natural opalescence which makes any direct spectrophotometric measurement impossible.

The medium must first be rendered transparent by the application of a preliminary treatment which confers on the medium a low absorbance, less than 0.1 optical density unit over the range 400 to 800 nm.

In the case of milk, for example, the observed stability is due essentially to the presence of calcium phosphocaseinates and fat globules.

Reagents consisting of mixtures of solvents have been suggested for the dissolution of the colloidal components.

Thus, Bosset et al. have studied the complete dissolution of milk by the use of mixed solvents such as the mixtures sodium hydroxide/water/n-butylamine or sodium hydroxide/water/tetrahydrofuran (see literature references (1) and (2) at the end of this description).

These solvents make it possible to determine the total proteins of milk by the so-called Biuret method, but have the disadvantage of making necessary a high dilution of the milk.

Another reagent for making milk transparent has been described by Linden et al. (3). This reagent, called hereafter the Linden reagent, consists of a mixture of n-butylamine/cyclohexanone/octylphenyl polyoxyethylene ether (such as those marketed under the trade name Triton X). It has the advantage of rapidly making milk transparent whilst diluting it only slightly. Nonetheless, the viscosity, even of the final transparent mixture, is high, of the order of 1.1 P at 20° C., and this makes the mixture difficult to handle. Furthermore, it proves to be a quite aggressive solvent towards the polymers of plastic materials. Thus, measuring instruments made of such polymers cannot be used. This solvent also exerts an aggressive action towards the bacteria present in the biological medium. Thus, measurements must be made quickly before the cells lyse. Moreover, the composition of the reagent itself prohibits its use for the measurement of certain parameters. Hence, it is not suitable for the determination of the concentration of amino groups in a sample since the reagent itself contains an amine which can interfere with the measurement of amino groups in the sample.

The progress of the experimental studies of the investigators in this domain has led them to develop a new reagent which can be employed to render transparent any biological medium existing in the form of an emulsion or a suspension, including milk. This reagent does not contain n-butylamine, a principle constituent of the Linden reagent described above, but consists of a combination of components which enables advantageous new effects to be obtained. In particular, the inventors have observed that the combined use of certain constituents furnishes a reagent for making media transparent which possesses greater stability, is less aggressive and less viscous and which obviates the difficulties associated with the determination of certain chemical functions in the biological media.

Thus, the aim of the invention is to provide a new reagent which instantaneously clarifies the turbidity of a given biological medium and which is easier to handle owing to a reduced viscosity and a very high stability.

The invention also relates to the application of this reagent for carrying out biological, chemical and physical analyses of opalescent biological media, more especially foodstuffs or suspensions obtained from foodstuffs or even from cosmetics.

The reagent of the invention designed to render media transparent, based on of a mixture of solvents, is characterized in that it contains in combination:

an aliphatic ketone constituting a lipophilic solvent, soluble in aqueous media, stable and enabling measurements to be made in the near UV, a detergent acting as solubilizing agent and consisting of a non-ionic polyoxyalkylene derivative or an amphoteric alkaline salt, a base and/or a surface active agent possessing the property of denaturing the conformational structures of components of the biological medium to be analyzed.

In an advantageous manner, the use of these elements in combination gives rise to a reagent which instantaneously clarifies a given medium and which possesses improved stability compared with other known reagents.

Furthermore, it will be observed that this reagent does not contain n-butylamine, making it possible to avoid both the inconvenience of the odour of this substance and any interference it may cause in the determination of the concentration of the amines present in the media one wishes to study. Unlike the known reagents, it does not bring about hydrolysis of the Ellman reagent, dithio-bis-2-nitrobenzoic acid or DTNB, and thus enables the concentration of SH or of S-S groups to be determined in milk, for example.

The aliphatic ketone is chosen preferably from among the ketones possessing a dielectric constant, $\Sigma$, of the order of 18.5. These are comprised, in particular, by ketones with a linear chain containing not more than 4 carbon atoms. A preferred ketone is constituted by butanone-2. This ketone offers the advantage of a relatively low density combined with a high solubility in water.

Another appropriate ketone is constituted by pentane-dione.

The agent acting as detergent is a non-ionic polyoxyalkylene derivative of the ether, alcohol or ester type or an amphoteric alkaline salt. This agent acts to promote the miscibility of the aqueous phases, containing the proteins, with the liped phases. A particularly preferred derivative is polyethylene glycol-4-tert-octylphenyl ether, such as that marketed under the trade name of Triton X. This product offers the advantage of being the least powerful denaturant, the most readily available and inexpensive.

Other polyoxyalkylene derivatives are however suitable, among which may be cited:

a nonyl phenoxypolethoxyethanol derivative such as that marketed under the trade name of Triton N, a polyethylene glycol ether derivative such as that marketed under the trade name of Brij, a polyoxyethylene sorbitol ester derivative such as that marketed under the trade name of Tween, a polyoxyethylene glycol ester of a fatty acid (monolaurate) such as that marketed under the trade name of Span.

As regards amphoteric alkaline salts, mention may be made of sodium desoxycholate and lithium diiodosalicylate.

As indicated above, the reagent of the invention also includes a base and/or a denaturating agent, in combination with the lipophilic solvent and the detergent defined in the previous paragraph. The base is preferably constituted by sodium hydroxide. It is, in fact, observed that sodium ions exert a favorable effect on the disaggregation of the micelles of the proteins of the biological medium to be analyzed and solubilizes them. The denaturating agent is a sodium salt, preferably sodium dodecyl sulfate. A substance of this kind makes it possible to neutralise the electrical charges on the proteins and this leads to the interactions between them being suppressed.

According to a preferred embodiment of the invention, the reagent designed to make biological media transparent consists of butanone-2, Triton X, sodium hydroxide and/or sodium dodecyl sulfate. The combining of these components leads to a reagent which is stable at room temperature and which can be easily stored in a frozen state.

When brought into contact with the reagent, the biological medium to be studied is also observed to exhibit great stability, thus allowing adequate time for the necessary series of measurements.

Another advantage of the reagent lies in its viscosity of about 0.97 P at 20° C. which is thus reduced with respect to that of the reagent containing n-butylamine of the prior art described above.

The relative proportions of these components are adjusted as a function of the concentration of proteins and lipids in the biological medium to be analyzed. Thus, in the case of a medium poor in lipids, the concentration of the lipophilic solvent may be considerably reduced. Generally speaking, the amounts of lipophilic solvent and detergent are adjusted with respect to each other. Similarly, the amount of base is adjusted with respect to that of the denaturating agent. One of these groups, namely the lipophilic solvent and the detergent on the one hand and the base and/or denaturant agent on the other, is present in amount varying from not less than 15% to not more than 85%. A suitable clarification of a medium is produced by first mixing 15% to 85% by volume of the lipophilic solvent with 85% to 15% by volume of the detergent. The base is used at a concentration of 0 to 0.5N and the denaturating agent at 15% to 0% by volume.

Owing to its high dissolving power, the reagent of the invention proves to be particularly suited to rendering biological media transparent for the purpose of analysis. In fact, it leads to a complete dissolution of the protein and lipid constituents and entails only slight dilution of the medium. It is thus possible to carry out specrophotometric measurements directly and rapidly even in the near UV region in view of its low absorbance between 330 and 800 nm.

The following are some of the analytical application which may be mentioned:

the titration of specific groups, such as amino functions in order to study, in particular, the maturing of soft cheese, sulfhydryl groups and disulfide bridges in order to assess the degree of heating of a sample, and mineral constituents such as Ca, Fe, Mg, Cl or $NO_3$, the determination of enzymatic activities in milk and milk products, for example, such as alkaline phosphatase and peroxidase in order to monitor a thermal treatment, and of proteases and $\beta$-D-galactosidase in order to check the quality of a starting material, the counting of the micro-organisms present in a medium with their identification, the study of the growth curves of the bacteria. Such studies are particularly useful for assessing the rate of growth of lactic acid bacteria in leaven in the dairy industry, for identifying, by image analysis, certain bacterial strains after milks, leavens, yogourts or other milk products had been made transparent, and for demonstrating the aggressiveness of the clarifying reagent towards the bacteria (as observed in the electron microscope, lysis of cells appears to be much less rapid than with the known clarifying reagents).

Such measurements may be carried out for the purposes of verifying the absence of toxic substances in any product containing proteins and lipids, especially foodstuffs such as milk products, whole milk, skimmed milk, half-skimmed milk, dried milk, whey, cheeses, leavens, meat products, emulsions of the oil-in-water type and even cosmetic products, especially cosmetic creams.

BRIEF DESCRIPTION OF THE DRAWINGS

Other properties and advantages of the invention will become apparent in the examples which follow and by making reference to FIGS. 1 and 5:

FIG. 2 presents the curves relating to the spectral properties of different industrial milks after they have been made transparent.

EXAMPLE 1

Preparation of a clarifying reagent and its application to the analysis of milk.

A reagent composed of the following quaternary mixture is prepared:

0.1N sodium hydroxide,
butanone -2,
Triton X-100,
1% SDS.

2 ml of this mixture are added to a test tube containing 1 ml of a sample of skimmed milk or semi-skimmed milk, or 0.5 ml of a sample of whole milk or 1 ml of a suspension of a milk product in hot water (yogourts at 10%, cream cheeses at 10%, soft or pressed cheeses at 5%, emulsified cream at 5%). Incubation is carried out for 2 to 5 min. in a water-bath at 37° C.±1.

The residual absorption in the case of skimmed milk varies from 0.010 to 0.098 between 800 and 330 nm and consequently it is possible to carry out colorimetric reactions which can be read by means of a molecular absorption spectrometer.

Figure 1A:
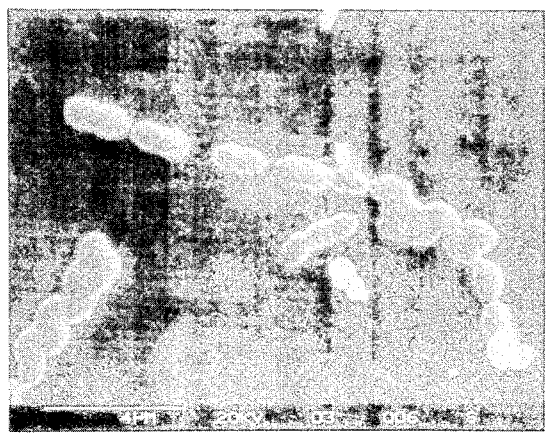
FIG. 1(a-c) presents photographs of lactic acid bacteria before treatment and 1 hour after treatment with the Linden reagent and with the reagent of the invention, respectively.
Figure 1B:
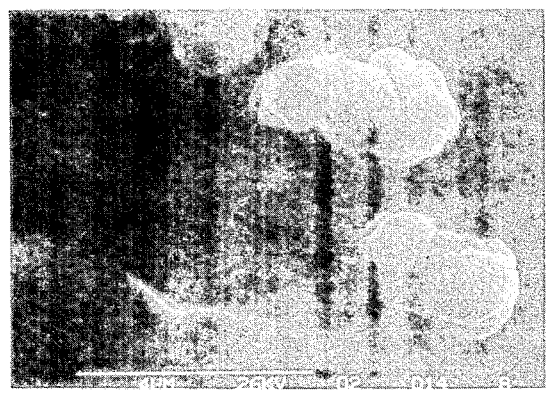
Figure 1C:

FIG. 1 present photographs of (a) Streptococcus thermophilus CNRZ 302 bacteria present in milk, (b) these bacteria 1 hour after treatment with the Linden reagent of the prior art, (c) the same bacteria 1 hour after treatment with the reagent of the invention.

The results obtained show that the bacteria are scarcely lysed when the reagent of the invention is used (see photograph 1c) whereas lysis appears to be quite marked in the photograph 1b which was taken after treatment of the bacteria with the known reagent. These results thus demonstrate the mildness of the reagent of the invention.

FIG. 2 presents the curves illustrating the spectral properties of the different industrial milks which have been treated with the reagent. Curve 1 represents the spectrum of the reagent itself and the curves, 2, 3 and 4 those of the spectra of a skimmed fresh milk, a skimmed UHT milk and a skimmed over-heated milk. Examination of these curves shows that the reagent of the invention exhibits low absorbance.

EXAMPLE 2

Application of the reagent of example 1 for the determination of enzymes in milk.

APPLICATION TO THE DETERMINATION PHOSPHATASE ACTIVITY:

1. Principle

Alkaline phosphatase hydrolyzes its substrate disodium p-nitrophenylphosphate. The release of p-nitrophenol is monitored by spectroscopy after all of the components of the reaction mixture have been completely dissolved by the reagent of the invention.

2. Reagents

The following reagents are used:

aqueous solution of $24.3 \times 10^{-3}$M diethanolamine buffer, pH 10.6, substrate: $5 \times 10^{-3}$M p-nitrophenylphosphate final concentration in the buffer solution described immediately above, reagent of example 1.

3. Procedure

A 0.5 ml sample of milk, diluted to 1/100, and 1 ml of substrate solution are introduced into a test tube. The contents of the tube are shaken and incubated at 37° C. for 15 min., then 2 ml of the reagent are added. The reaction mixture is shaken and the extinction of the solution at 420 nm is read at 5 min. intervals at 37° C.

4. Expression of the results

A sample which has not been incubated serves as reference: Phosphatase activity is expressed in $\mu$ mole of p-nitrophenol released per ml of milk as a function of time. The mean value found for 22 samples taken from a large variety of milks is about 55 $\mu$ moles of p-nitrophenol released/ml of milk/15 min.

Application to the determination of peroxidase activity:

1. Principle

This method is based on the decomposition of hydrogen peroxide by peroxidase and the binding of atomic oxygen to an acceptor. The measurement of the dye thus produced is performed by spectroscopy after the various constituents of the reaction mixture have been completely dissolved by the reagent of the invention.

2. Reagents

The following reagents are used:

a filtered 2% aqueous solution of p-phenylene diamine 2HCl (P.P.D.).

a 10% V/V solution of hydrogen peroxide, 3.1M aqueous solution of NaOH, reagent of example 1 with an apparent pH of 13.7.

3. Procedure

The pH of P.P.D. is brought to 7 by the addition of the aqueous solution of NaOH. A 0.5 ml sample of milk, diluted to 1/10 is introduced into a test tube and 0.5 ml of the P.P.D. solution, pH 7, is added, followed by 0.2 ml of the $H_2O_2$ solution. The mixture is shaken and then 0.2 of the NaOH solution and 2 ml of the reagent of the invention are added. The mixture is shaken and the extinction of the solution at 470 nm is read at 37° C. A sample of boiled milk which has been subjected to the same procedure serves as reference.

4. Results

The measurement of peroxidase activity is expressed in arbitrary units of activity per ml of milk as a function of time. One arbitrary unit per ml of milk corresponds to an increase of the absorbance by 1/1000 of an optical density unit under the operating conditions used. The mean value observed for 22 samples of a great variety of milks was 410 units Application to the determination of protease activity by using specific synthetic substrates 1. Principle Proteolytic activities are demonstrated by the use of various synthetic substrates belonging to the class of the 4-nitroanilides, which are hydrolyzed during the incubation. Measurement is made by means of a spectrometer after total dissolution of the reaction mixture by the reagent of the invention.

2. Reagents

The following reagents are used:

buffer solution, pH 8:

0.094M triethanolamine, 0.02% sodium azide solution.

substrates: L-alamine-4-nitroanilide or N-acetyl-L-alamine-4-nitroanilide, for example. The substrate is dissolved in the buffer to give a final concentration of $5 \times 10^{-3}$M.

the reagent of example 1.

3. Procedure

A 0.5 ml sample of milk and 1.5 ml of substrate solution are introduced into a test tube. The mixture is shaken and allowed to incubate for 0 to 24 hours at 37° C. 2 ml of the reagent of the invention are added, the mixture is shaken and left to stand at 37° C. for 15 min. The extinction of the solution at 410 nm is read at 37° C.

4. Expression of the results

A sample subject to the same procedure but without incubation serves as reference. The results are expressed in $\mu$ moles of 4-nitroaniline released per ml of milk as a function of time. The mean value found for 22 samples of a great variety of milks is about:

1000 $\mu$ mole/ml of milk/24 h for the substrate L-alanine-4-nitroanilide,

800 $\mu$ mole/ml of milk/24 h for the substrate N-acetyl-L-alanine-4-nitroanilide.

EXAMPLE 3

Application of the reagent of example 1 to the determination of sulfhydryl groups in milks.

To a 1 ml sample (milk diluted to ½ in 1 nM Tris- 92 nM Gly buffer, pH 8) is added 1 ml of 8M urea (in the pH 8 buffer), followed by 50 $\mu$l of the DTNB reagent (4 mg of 5.5'-dithio-bis-2-nitrobenzoate per ml). The reaction mixture is incubated for 10 min. at room temperature and then 2 ml of the transparency-producing reagents are added with shaking. The mixture is left to stand for 2 min. at 37° C. and then it is read at 412 nm at intervals of 20 min.

The following results are obtained:
skimmed fresh milk: 1.90 µg SH/g of milk,
skimmed instant milk: 1.47 µg SH/g of milk,
skimmed UHT milk: 0.55 µg SH/g of milk.

EXAMPLE 4

Application of the reagent of example to the determination of $NH_2$ groups in milks and cheeses.

To 1 ml of sample (milk diluted to 1/10, 1% suspension of cheese in warm water) is added 1 ml of the TNBS reagent (0.1% trinitrobenzene sulfonic acid in 4% $NaHCO_3$ pH 8. The mixture is incubated for 2 h at 37° C. and then 1 ml of 4% $NaHCO_3$ buffer, pH 8.5, is added followed by 0.5 ml of 0.1 N HCl and 1.5 ml of the transparency-producing reagent. The mixture is shaken and left to stand for 2 min. at 37° C. and then read at 420 nm at intervals of 30 min.

Figure 3:
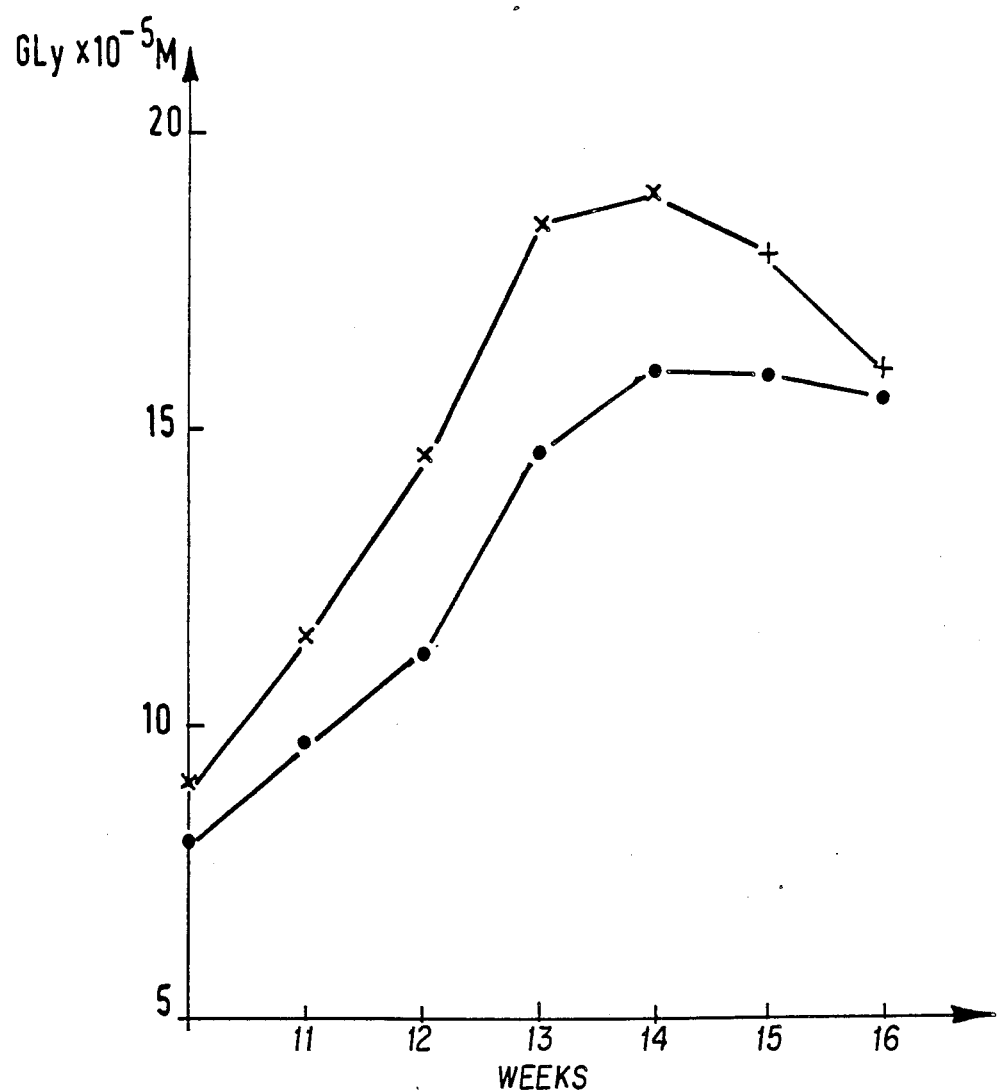
FIG. 3 shows the curve obtained on analysis of the concentration of $NH_2$ groups in cheeses, and, FIGS. 4 and 5 represent the spectrophotometric and nephelometric curves for the growth rate of lactic acid bacteria, respectively.

FIG. 3 presents the curves for the measurement of the concentration of $NH_2$ group in a Brie made by pasteurized milk (curve x—x) and a Brie made from raw milk (curve.—.) a week compared with the concentration of $NH_2$ groups of glycine expressed in meq. $\times 10^{-5}$ M. (In a standard manner, the results obtained with each solution of Brie are assessed by comparing them with a calibration curve established with glycine under the same experimental conditions.

In an advantageous manner, such a determination of the concentration of $NH_2$ group can be carried out by using the reagent of the invention designed to render transparent an opalescent biological medium.

EXAMPLE 5

Estimation of the rate of growth of bacteria.

Figure 5:
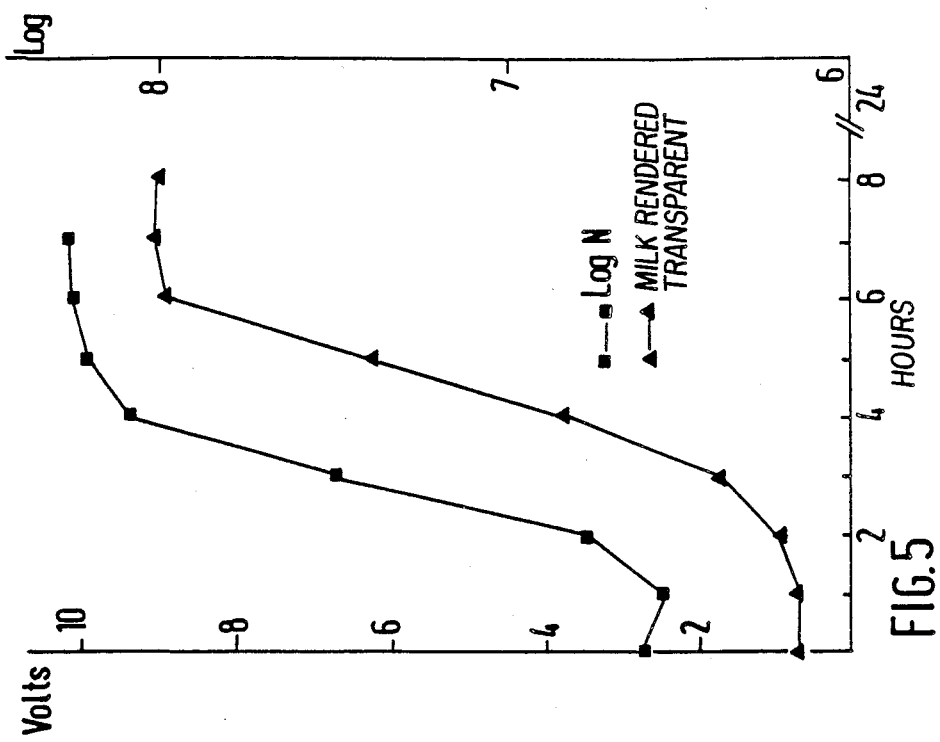
Figure 4:
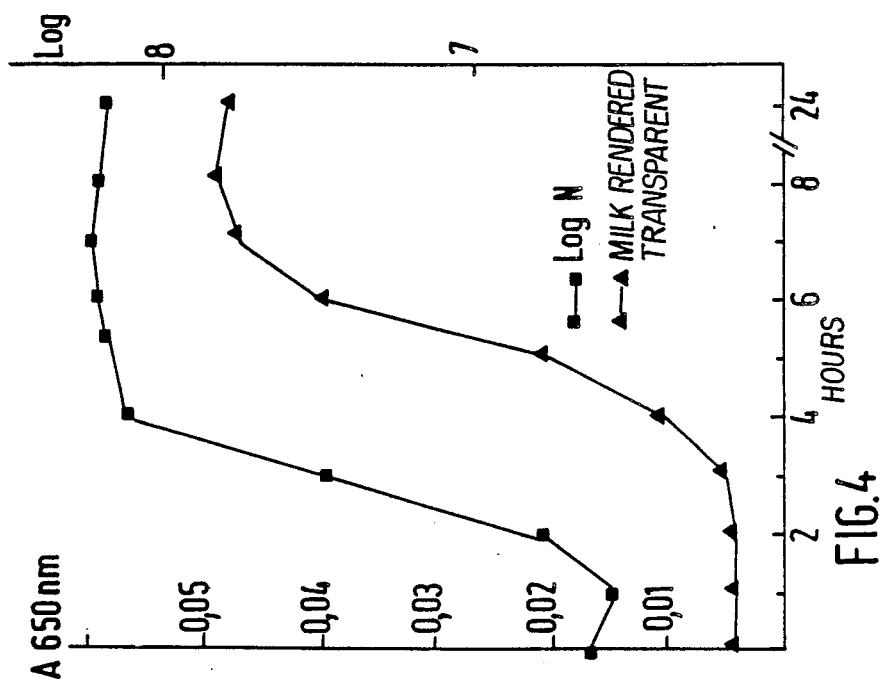

FIGS. 4 and 5 present the results obtained with Streptococcus thermophilus CNRZ 302 under the conditions described by Kouomegne et al. (4). FIG. 4 presents the measurement of the optical density at 650 nm as a function of time in hours, and FIG. 5 presents the measurement of the voltage recorded in laser nephelometry as a function of time in hours. In these figures, the curves ■—■ correspond to the logarithm of the number of bacteria counted as a function of time and the curves ▲—▲ to the measurements performed on milk treated with the reagent of the invention. The results illustrated by these curves show that it is possible to obtain a rapid estimation of the number of bacterial present in the milk.

LITERATURE REFERENCE (1) Bosset J. O. Blanc, B. H. and Plattner E. Trav. Chim. Aliment. Hyg. (1977), 68 225–239.

(2) Bosset, J. O. Blanc B. H. and Plattner E., Trav. Chim. Aliment. Hyg. (1977), 68, 504–512.

(3) Linden G, Humbert G, Desnouveaux R. and Picard J. Le Lait (1982), 62, 209–219.

(4) Kouomegne R., Bracquart P; and Linden G, Le Lait (1984), 64, 418–435.

We claim:

1. A reagent for rendering transparent a protein and lipid-containing mixture comprising:
   an aliphatic ketone that is a lipophilic solvent and soluble in aqueous media and that makes possible measurements in a near UV-like region;
   a non-ionic polyoxyalkylene detergent or an amphoteric alkaline salt detergent;
   a hydroxide base; and
   an organic sodium salt surface active agent which can denature the protein- and lipid-containing mixture.

2. The reagent of claim 1, wherein the ketone possesses a dielectric constant of the order of 18.5.

3. The reagent of claim 2, wherein the ketone is a linear chain ketone containing up to 4 carbon atoms.

4. The reagent of claim 3, wherein the ketone is 2-butanone.

5. The reagent of claim 1, wherein the detergent is a non-ionic polyoxyalkylene derivative of an ether, alcohol or ester.

6. The reagent of claim 5, wherein the detergent is a polyethylene glycol-4-tert-octylphenyl ether.

7. The reagent of claim 5, wherein the detergent is a nonylphenoxypolyethoxyethanol derivative, a polyethylene glycol derivative, a polyoxyethylene sorbitol ester derivative or a polyoxyethylene glycol ester of a fatty acid.

8. The reagent of claim 1, wherein the detergent is an amphoteric alkaline salt.

9. The reagent of claim 8, wherein the detergent is sodium desoxycholate or lithium diiodosalicylate.

10. The reagent of claim 1, wherein the base is sodium hydroxide.

11. The reagent of claim 1, wherein the sodium salt is sodium dodecyl sulfate.

12. The reagent of claim 1, comprising 2-butanone, a polyethylene glycol-4-tert-octylphenyl ether, sodium hydroxide and sodium dodecyl sulfate.

13. The reagent of claim 1, comprising 15% to 85% by volume of the ketone, 85% to 15% by volume of the detergent, 0 to 0.5N of the base and 15% to 0% by volume of the surface active agent.

14. In a method for analyzing a protein-and lipid-containing mixture, the improvement comprising the step of treating the mixture with the reagent of claim 1.

15. The method of claim 15, wherein the mixture is a milk product, a whey, a cheese, a leaven, a meat product, an oil-in water emulsion, or a cosmetic.

* * * * *

UNITED STATES PATENT AND TRADEMARK OFFICE
CERTIFICATE OF CORRECTION

PATENT NO. : 4,981,610

DATED : January 1, 1991

INVENTOR(S) : Linden, Guy et al.

It is certified that error appears in the above-identified patent and that said Letters Patent is hereby corrected as shown below:

On the title page, in item [75], delete the 2nd and 3rd Inventor's city name "Jarville La Mai" and "Nancy", and insert --Jarville La Malgrange-- and --Yaounde, Cameroun--.

Signed and Sealed this

Eighteenth Day of August, 1992

*Attest:*

DOUGLAS B. COMER

*Attesting Officer*     *Acting Commissioner of Patents and Trademarks*